US010143452B2

United States Patent
Golan

(10) Patent No.: US 10,143,452 B2
(45) Date of Patent: Dec. 4, 2018

(54) FRACTURING CALCIFICATIONS IN HEART VALVES

(71) Applicant: PI-R-SQUARED LTD., Rehovot (IL)

(72) Inventor: Erez Golan, Rehovot (IL)

(73) Assignee: Pi-Cardia Ltd., Rehovot (IL)

( * ) Notice: Subject to any disclaimer, the term of this patent is extended or adjusted under 35 U.S.C. 154(b) by 626 days.

(21) Appl. No.: 14/362,405

(22) PCT Filed: Dec. 5, 2012

(86) PCT No.: PCT/US2012/067812
§ 371 (c)(1),
(2) Date: Jun. 3, 2014

(87) PCT Pub. No.: WO2013/085934
PCT Pub. Date: Jun. 13, 2013

(65) Prior Publication Data
US 2014/0316428 A1    Oct. 23, 2014

Related U.S. Application Data

(60) Provisional application No. 61/566,766, filed on Dec. 5, 2011.

(51) Int. Cl.
*A61B 17/22* (2006.01)
*A61B 17/00* (2006.01)
*A61B 17/3207* (2006.01)

(52) U.S. Cl.
CPC .. *A61B 17/00234* (2013.01); *A61B 17/22031* (2013.01); *A61B 17/3207* (2013.01); *A61B 2017/22098* (2013.01)

(58) Field of Classification Search
CPC .......... A61B 17/00234; A61B 17/3207; A61B 17/22031; A61B 2017/22098
(Continued)

(56) References Cited

U.S. PATENT DOCUMENTS 5,846,251 A * 12/1998 Hart ................ A61B 17/22031
606/127
7,179,275 B2 * 2/2007 McGuckin, Jr. .......... A61F 2/01
606/200

(Continued)

FOREIGN PATENT DOCUMENTS

WO    WO 2010014515 A2 *  2/2010    ....... A61B 17/22012
WO       2011/069025       6/2011

OTHER PUBLICATIONS

PCT Written Opinion PCT/2012/067812, dated Apr. 2, 2013.

*Primary Examiner* — Amy R Weisberg
(74) *Attorney, Agent, or Firm* — Dekel Patent Ltd.; David Klein

(57) ABSTRACT

A device for fracturing calcifications in heart valves characterized by a stabilizer assembly and an impactor assembly assembled on and deployed by a delivery system, wherein said delivery system is operable to cause relative motion between said impactor assembly and said stabilizer assembly with sufficient energy so as to fracture a calcification located in tissue which is sandwiched between said stabilizer assembly and said impactor assembly, wherein said impactor assembly and said stabilizer assembly have shaped impact delivery portions of which the footprint on the valve leaflets is shaped in accordance with a shape of desired fracture sites.

6 Claims, 16 Drawing Sheets

(58) Field of Classification Search
USPC .................................. 606/108, 128, 133, 200
See application file for complete search history.

(56) References Cited

U.S. PATENT DOCUMENTS

| | | | |
|---|---|---|---|
| 7,803,168 B2* | 9/2010 | Gifford | A61B 17/22012 |
| | | | 600/462 |
| 7,931,659 B2* | 4/2011 | Bose | A61B 17/22 |
| | | | 606/113 |
| 8,092,470 B2* | 1/2012 | Miyamoto | A61B 17/22 |
| | | | 606/114 |
| 9,364,255 B2* | 6/2016 | Weber | A61B 17/320725 |
| 9,510,930 B2* | 12/2016 | Patel | A61F 2/01 |
| 2001/0041909 A1* | 11/2001 | Tsugita | A61F 2/013 |
| | | | 606/200 |
| 2002/0173819 A1* | 11/2002 | Leeflang | A61B 17/22 |
| | | | 606/200 |
| 2003/0004536 A1* | 1/2003 | Boylan | A61F 2/01 |
| | | | 606/200 |
| 2003/0023265 A1* | 1/2003 | Forber | A61F 2/013 |
| | | | 606/200 |
| 2003/0055452 A1* | 3/2003 | Joergensen | A61F 2/013 |
| | | | 606/200 |
| 2003/0139765 A1* | 7/2003 | Patel | A61F 2/01 |
| | | | 606/200 |
| 2003/0176884 A1* | 9/2003 | Berrada | A61F 2/013 |
| | | | 606/200 |
| 2004/0093017 A1* | 5/2004 | Chanduszko | A61B 17/0057 |
| | | | 606/200 |
| 2004/0230220 A1* | 11/2004 | Osborne | A61F 2/01 |
| | | | 606/200 |
| 2005/0015111 A1* | 1/2005 | McGuckin, Jr. | A61F 2/01 |
| | | | 606/200 |
| 2005/0043757 A1* | 2/2005 | Arad | A61B 17/0401 |
| | | | 606/200 |
| 2005/0075662 A1* | 4/2005 | Pedersen | A61B 17/22 |
| | | | 606/194 |
| 2005/0267515 A1* | 12/2005 | Oliva | A61F 2/01 |
| | | | 606/200 |
| 2006/0015137 A1* | 1/2006 | WasDyke | A61F 2/01 |
| | | | 606/200 |
| 2006/0036279 A1* | 2/2006 | Eidenschink | A61F 2/01 |
| | | | 606/200 |
| 2006/0095068 A1* | 5/2006 | WasDyke | A61F 2/01 |
| | | | 606/200 |
| 2006/0178695 A1* | 8/2006 | Decant, Jr. | A61B 5/02007 |
| | | | 606/200 |
| 2006/0287668 A1* | 12/2006 | Fawzi | A61F 2/013 |
| | | | 606/200 |
| 2007/0032816 A1* | 2/2007 | O'Connell | A61F 2/01 |
| | | | 606/200 |
| 2007/0112371 A1* | 5/2007 | Cangialosi | A61F 2/013 |
| | | | 606/200 |
| 2007/0112374 A1* | 5/2007 | Paul, Jr. | A61F 2/013 |
| | | | 606/200 |
| 2007/0135832 A1* | 6/2007 | Wholey | A61F 2/013 |
| | | | 606/200 |
| 2007/0191878 A1* | 8/2007 | Segner | A61F 2/01 |
| | | | 606/200 |
| 2007/0197858 A1 | 8/2007 | Goldfarb | |
| 2007/0198050 A1* | 8/2007 | Ravenscroft | A61F 2/01 |
| | | | 606/200 |
| 2007/0233174 A1* | 10/2007 | Hocking | A61F 2/013 |
| | | | 606/200 |
| 2008/0234722 A1* | 9/2008 | Bonnette | A61F 2/013 |
| | | | 606/200 |
| 2008/0275487 A1* | 11/2008 | Fleming | A61F 2/01 |
| | | | 606/200 |
| 2008/0275489 A1* | 11/2008 | Kinst | A61F 2/01 |
| | | | 606/200 |
| 2008/0275492 A1* | 11/2008 | Farmiga | A61F 2/01 |
| | | | 606/200 |
| 2008/0275495 A1* | 11/2008 | Silver | A61F 2/01 |
| | | | 606/200 |
| 2008/0306499 A1* | 12/2008 | Katoh | A61B 17/22 |
| | | | 606/159 |
| 2009/0198270 A1* | 8/2009 | McGuckin, Jr. | A61F 2/01 |
| | | | 606/200 |
| 2010/0049239 A1* | 2/2010 | McGuckin, Jr. | A61F 2/01 |
| | | | 606/200 |
| 2010/0198211 A1* | 8/2010 | Kassab | A61B 17/320725 |
| | | | 606/32 |
| 2010/0268264 A1* | 10/2010 | Bonnette | A61B 17/221 |
| | | | 606/200 |
| 2010/0312269 A1* | 12/2010 | McGuckin, Jr. | A61F 2/01 |
| | | | 606/200 |
| 2011/0060359 A1* | 3/2011 | Hannes | A61B 17/22031 |
| | | | 606/200 |
| 2011/0118634 A1* | 5/2011 | Golan | A61B 17/22012 |
| | | | 601/4 |
| 2012/0059356 A1* | 3/2012 | di Palma | A61B 17/221 |
| | | | 604/509 |
| 2012/0245607 A1* | 9/2012 | Gershony | A61B 17/320725 |
| | | | 606/159 |
| 2013/0035713 A1* | 2/2013 | Snow | A61F 2/01 |
| | | | 606/200 |
| 2013/0053882 A1* | 2/2013 | Hocking | A61B 17/221 |
| | | | 606/200 |
| 2013/0274793 A1* | 10/2013 | McGuckin, Jr. | A61F 2/01 |
| | | | 606/200 |
| 2014/0012310 A1* | 1/2014 | Urbanski | A61F 2/01 |
| | | | 606/200 |
| 2015/0265299 A1* | 9/2015 | Cooper | A61B 17/221 |
| | | | 606/200 |
| 2016/0008121 A1* | 1/2016 | Inoue | A61F 2/013 |
| | | | 606/200 |

* cited by examiner

FRACTURING CALCIFICATIONS IN HEART VALVES

FIELD OF THE INVENTION

The present invention generally relates to devices and methods for fracturing calcifications in heart valves, such as aortic valve leaflets.

BACKGROUND OF THE INVENTION

Essential to normal heart function are four heart valves, which allow blood to pass through the four chambers of the heart in the proper flow directions. The valves have either two or three cusps, flaps, or leaflets, which comprise fibrous tissue that attaches to the walls of the heart. The cusps open when the blood flow is flowing correctly and then close to form a tight seal to prevent backflow.

The four chambers are known as the right and left atria (upper chambers) and right and left ventricles (lower chambers). The four valves that control blood flow are known as the tricuspid, mitral, pulmonary, and aortic valves. In a normally functioning heart, the tricuspid valve allows one-way flow of deoxygenated blood from the right upper chamber (right atrium) to the right lower chamber (right ventricle). When the right ventricle contracts, the pulmonary valve allows blood to flow from the right ventricle to the pulmonary artery, which carries the deoxygenated blood to the lungs. The mitral valve, allows oxygenated blood, which has returned to the left upper chamber (left atrium), to flow to the left lower chamber (left ventricle). When the left ventricle contracts, the oxygenated blood is pumped through the aortic valve to the aorta.

Certain heart abnormalities result from heart valve defects, such as is stenosis or calcification. This involves calcium buildup in the valve which impedes proper valve leaflet movement.

SUMMARY OF THE INVENTION

The invention consists of minimally invasive devices and methods that may be used for fracturing calcifications in aortic valve leaflets, in order to increase leaflet pliability and mobility, thereby increasing the cross-sectional area of the open valve in patients with aortic stenosis. In addition, the devices and methods described can be applied as a preparation step for trans-catheter aortic valve implantation, in order to allow valve implantation in heavily calcified or asymmetrically calcified native valves, to increase the cross-sectional area of the implanted valve and to decrease the risk of paravalvular leaks. The devices and methods may also be used for fracturing calcifications in other valves, such as the mitral valve, for performing angioplasty on calcified plaque, or for fracturing hard deposits such as kidney or bladder stones.

The present invention seeks to provide improved devices and methods that may be used for fracturing calcifications in aortic valve leaflets, in order to increase leaflet pliability and mobility, either as standalone treatment, bridge treatment or preparation of the "landing zone" for trans-catheter valve implantation.

The term "fracture" refers to any kind of reduction in size or any modification in shape or form, such as but not limited to, fracturing, pulverizing, breaking, grinding, chopping and the like.

There is provided in accordance with an embodiment of the invention a device for fracturing calcifications in heart valves including a catheter including an external shaft in which are disposed an expandable stabilizer, an impactor shaft on which are mounted expandable impactor arms, and an internal shaft, characterised in that the internal shaft is movable to cause the impactor arms to expand outwards and be locked in an expanded shape, and wherein an impacting element is movable to cause the impactor arms, while in the expanded shape, to move towards the tissue with sufficient energy so as to fracture a calcification located in tissue which is fixed by the stabilizer in a certain position vis-à-vis the impactor arms.

In accordance with a non-limiting embodiment of the invention the impacting element includes the internal shaft which is connected to a distal portion of the impactor arms and which is operative to move relative to the impactor shaft to expand the impactor arms outwards and to cause the impactor arms, while in the expanded shape, to move towards the stabilizer with the sufficient energy. The internal shaft may be lockable relative to the impactor shaft so that the impactor arms are fixed.

In accordance with a non-limiting embodiment of the invention the impacting element includes a weight and a biasing device, wherein the biasing device urges the weight towards the impactor arms with the sufficient energy. In one example, the weight is mounted on the biasing device which is fixed to a distal tip of the catheter. In another example, the weight is fixed to the internal shaft of the catheter. In yet another example, the biasing device includes a pneumatic energy source connected to a pressurized air source.

In accordance with a non-limiting embodiment of the invention the stabilizer includes a stabilizer structure that includes one or more elements (of any form or shape, such as rods, loops or more complex structures) optionally covered by a stabilizer cover. The stabilizer may include a stabilizer structure covered by a covering balloon. An inflate/deflate tube may be inserted into the covering balloon. A first pressure sensor may be located near the stabilizer (in the portion of the catheter that lies in the aorta) and a second pressure sensor may be located near the impactor arms (in the portion of the catheter that lies in the LVOT or left ventricle). The device can be designed in a "reverse" manner for trans-apical use, so that the impactor is proximal and the stabilizer may be positioned at a distal tip of the device. Stabilizer arms may be expandable outwards from the external shaft.

BRIEF DESCRIPTION OF THE DRAWINGS

The present invention will be understood and appreciated more fully from the following detailed description, taken in conjunction with the drawings in which.

DETAILED DESCRIPTION OF EMBODIMENTS

Figure 1:
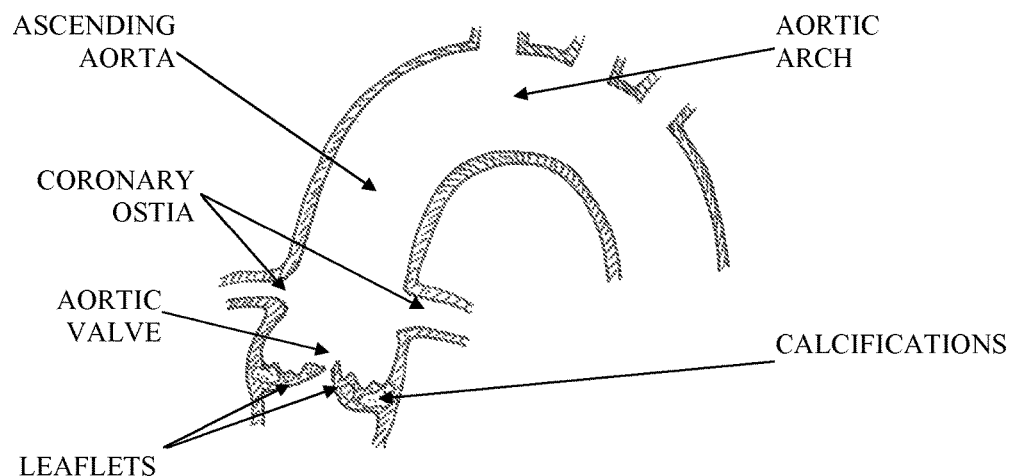
FIG. 1 is a simplified illustration of the anatomy of a calcified aortic valve, ascending aorta and aortic arch.

Reference is now made to FIG. 1, which illustrates the anatomy of a calcified aortic valve, ascending aorta and aortic arch. Calcifications may be embedded and/or superimposed on the valve leaflets, which are connected to the aortic wall just below the coronary ostia. Of course, the invention is not limited to these calcifications.

Figure 2:
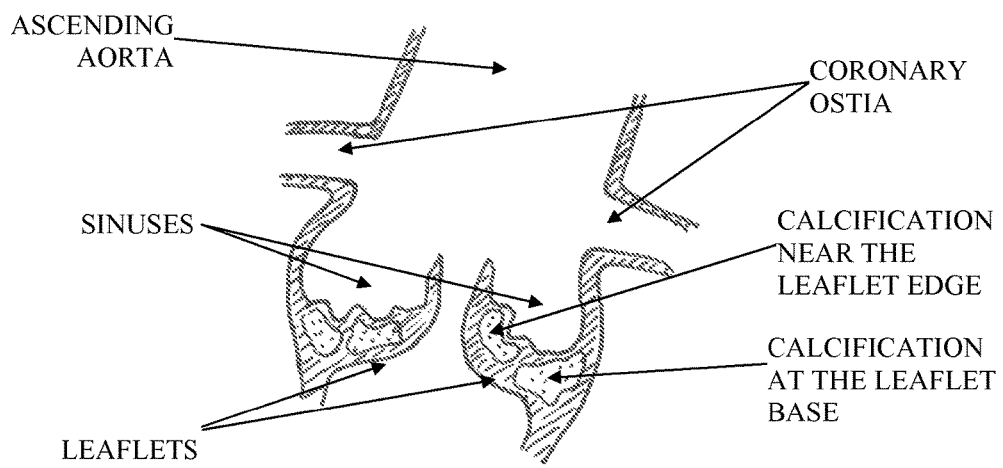
FIG. 2 is an enlarged view of a calcified aortic valve.

Reference is now made to FIG. 2, which illustrates a calcified aortic valve. The leaflets create concave sinuses on their aortic aspect, just below the coronary ostia. Calcification can be either embedded or superimposed on the leaflets, making the leaflets thicker and less pliable. Specifically, calcification that occurs at the leaflet base, i.e. where the leaflet connects to the annulus or aortic wall, can significantly impair the mobility of the leaflet.

Figure 3:
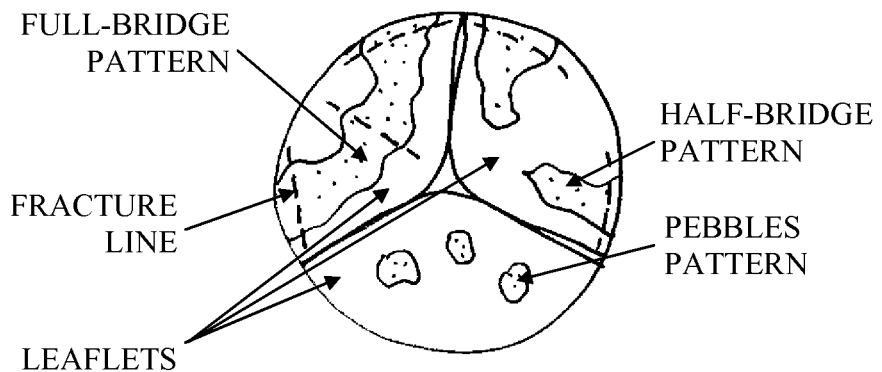
FIG. 3 is a simplified top-view illustration of typical calcification patterns on aortic valve leaflets.

Reference is now made to FIG. 3, which illustrates typical calcification patterns on aortic valve leaflets. A "full-bridge" pattern, "half-bridge" pattern and scattered "pebbles" are believed to be common forms of calcification in degenerated aortic stenosis of 3-leaflet valves, although the invention is not limited to any pattern. The dashed lines show the optimal fracture locations that need to be generated in order to maximize the increase in open valve cross sectional area during systole. These locations include the bases of the full-bridge and half-bridge patterns, close to the base of each leaflet, and the centerline of the leaflet in a full-bridge pattern. Leaflets with pebble patterns do not usually obstruct flow that much.

Figure 4:
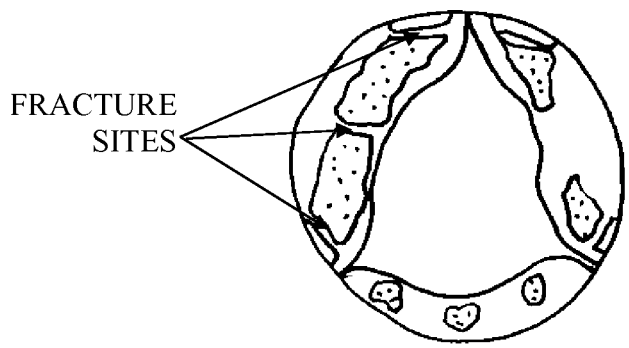
FIG. 4 is a simplified illustration of valve leaflets of FIG. 3 after fractures were obtained, in accordance with an embodiment of the invention.

Reference is now made to FIG. 4, which illustrates the valve leaflets of FIG. 3 after fractures were obtained. Both full-bridge and half-bridge patterns are broken into smaller segments, allowing the leaflets to open during systole, creating a significantly larger aortic valve area.

Figure 5:
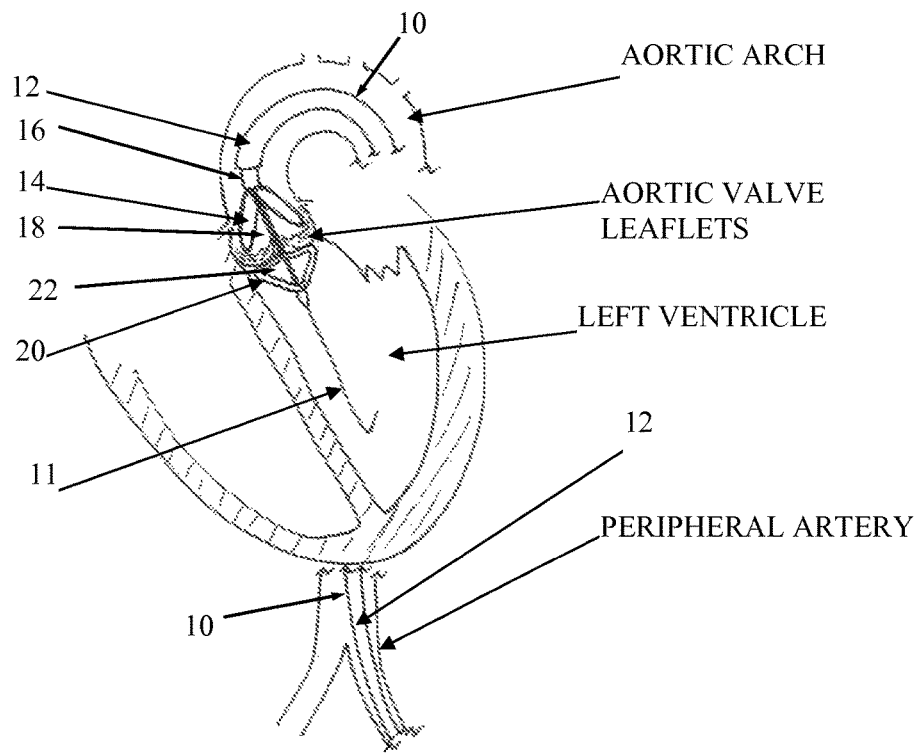
FIG. 5 is a simplified illustration of an impactor catheter delivered over a guidewire through a peripheral artery, over the aortic arch and into the aortic valve, described in PCT Patent Application PCT/US2010/058810 (WO 2011/069025).

Reference is now made to FIG. 5, which illustrates an impactor catheter delivered over a guidewire through a peripheral artery, over the aortic arch and into the aortic valve, described in PCT Patent Application PCT/US2010/058810 (WO 2011/069025), of the inventor (and assigned to the current assignee) of the present invention. An impactor element is opened below the aortic valve leaflets (ventricular aspect) and a stabilizer element is opened above the leaflets. Both elements preferably then "sandwich" the leaflets and the impactor is then pulled rapidly upwards to deliver mechanical impact to the valve leaflets, while the opposing stabilizer holds the leaflets and counteracts the force.

More specifically, a catheter 10 may be delivered over a guide-wire 11 through a vessel, such as the peripheral artery, using a retrograde approach, through the aortic arch and into the ascending aorta, just above the aortic valve. At this stage, all catheter components are still covered by a catheter external shaft 12. The external shaft 12 is then retracted so that an expandable (e.g., self-expanding) stabilizer 14, connected to a stabilizer shaft 16, opens up. Stabilizer 14 is used to guide, position and anchor the catheter distal part in the sinuses, just above the valve leaflets. It is noted that catheter 10 is just one example of a delivery system used to deliver and manipulate a stabilizer and impactor arms described below to impact calcifications. Optionally, the stabilizer and impactor arms described below may be delivered and/or manipulated by other devices other than a catheter, such as a guidewire or system of guidewires and push/pull wires.

An impactor shaft 18, including impactor arms 20, is then pushed forward (distally) through the center of the valve into the left ventricle. When pushed forward the impactor arms 20 are folded so that they can easily cross the valve. An internal shaft 22, which is connected to the distal portion of the impactor arms 20, is then pulled proximally to cause the impactor arms 20 to open (expand) outwards sideways and lock them in the expanded shape. Impactor and internal shafts 18 and 22 are then pulled back (proximally) a bit in order for the impactor arms 20 to make good contact with the ventricular aspect of the leaflets, so that the leaflets are "sandwiched" between the proximally-located stabilizer 14 (from above in the sense of the drawing) and the distally-located impactor arms 20 (from below in the sense of the drawing). In order to fracture leaflet calcifications, impactor arms 20 are pulled abruptly towards the leaflet tissue, while the stabilizer 14 holds the relevant portion of the leaflets in place, by pulling impactor and internal shafts 18 and 22 at a speed of at least 1 m/sec, such as without limitation, around 5-20 msec, but with an amplitude of at least 0.5 mm, such as without limitation, about 0.5-3 mm, so that calcification is fractured but soft tissue is unharmed. The delivery of the impactor and stabilizer elements can be done in a reverse manner. In such a case, the impactor first crosses the valve and is opened in order to position and center the device. The stabilizer is then opened in order to sandwich the leaflets, and then impact is delivered.

The present invention seeks to provide improved structure over that described in PCT/US2010/058810, both for impact and stabilization.

Figure 6:
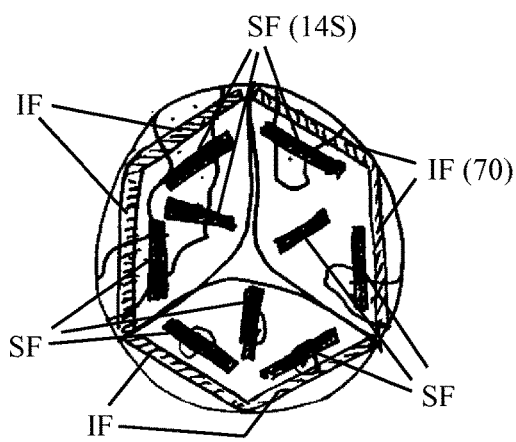
FIG. 6 is a simplified illustration of the valve leaflets of FIG. 3 with a footprint of both impactor and stabilizer elements on the leaflets, in accordance with an embodiment of the invention.

Reference is now made to FIG. 6, which illustrates the valve leaflets of FIG. 3 with a preferred footprint (although the invention is not limited to this footprint) of both impactor 70 and stabilizer elements 14S on the leaflets, in accordance with embodiments of the invention described hereinbelow. The impactor, when in an open position, preferably makes contact with the leaflets from below (the ventricular aspect), along the regions marked as "IF", short for "impactor-footprint". The stabilizer element (such as a stabilizer 80) preferably, but not necessarily, makes contact with the leaflets from above (the aortic aspect) along the regions marked as "SF", short for "stabilizer-footprint". The impactor and stabilizer elements can be brought closer together until the leaflets are "sandwiched" by both elements. The impactor is then pulled rapidly towards the stabilizer to deliver impact to the valve leaflets, creating a strong and rapid bending force between opposing elements that can generate fractures in the calcifications. Any variation in the impactor or stabilizer footprint, including an overlap/crossing of the footprints, increase or decrease of the diameter of the impactor or stabilizer, etc., is possible.

Figure 7:
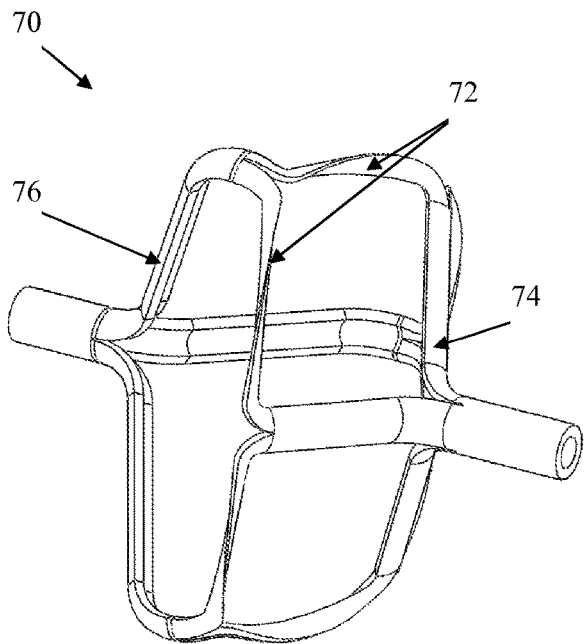
FIG. 7 is a simplified illustration of the "stent-like" impactor design with a footprint similar to the impactor footprint shown in FIG. 6, in accordance with an embodiment of the invention.

Reference is now made to FIG. 7, which illustrates an impactor assembly 70, having a "stent-like" impactor design, in accordance with an embodiment of the invention, with a footprint similar to the impactor footprint presented in FIG. 6. Impactor assembly 70 includes one or more impaction struts 72, which extend between proximal structural struts 74 and distal structural struts 76. The "stent-like" impactor preferably, but not necessarily, contacts the leaflets from their ventricular aspect using impaction struts 72. Impaction struts 72 run along the connection of the leaflet to the aortic wall, creating a footprint on an area that, if not because of calcific deposits, would be flexible enough to allow high mobility of the leaflets. The positions of distal structural struts 76 are illustrated at about 120° apart, but the invention is not limited to this spacing. Fractures along or near the footprint of the "stent-like" impactor results in a significant increase in aortic valve cross sectional area during systole. The "stent-like" impactor may be used in various rotational positions on the valve, preferably, but not necessarily, with proximal structural struts 74 on the ventricular aspect of the commissures, which is the "natural" rotational position of the impactor. Alternatively, the impactor can be rotated so that the proximal structural struts contact the centerline of the valve's leaflets.

Figure 8:
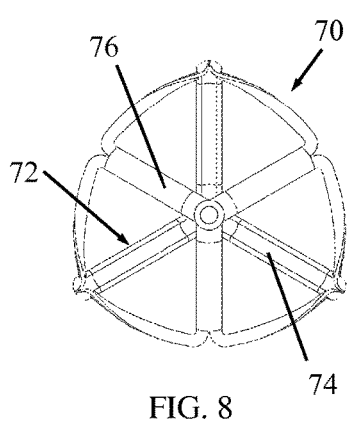
FIGS. 8-9 are top and side views, respectively, of the "stent-like" impactor, in accordance with an embodiment of the invention.
Figure 9:
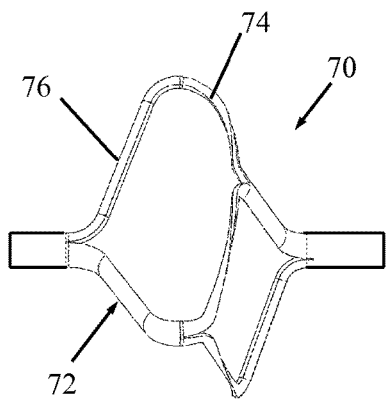

Reference is now made additionally to FIGS. 8 and 9, which illustrate more views of impactor assembly 70. The structure of the "stent-like" impactor is designed to allow active self-positioning of the device on the aortic valve. Proximal structural struts 74 are located higher than the impaction struts 72 and at an angle relative to the impaction struts 72, so that the proximal structural struts 74 position themselves just below the commissures when the impactor 70 is pulled towards the valve. The positioning of the proximal structural struts 74 below the commissures is due to stable equilibrium of mechanical forces and therefore cannot be mistakenly altered.

The impaction struts 72, as well as stabilizer 14S (FIG. 6), that is, the portions where the impact takes place, are preferably shaped in accordance with a shape of the desired fracture site, e.g., leaflet bases (close to the annulus) and central folding lines of the native valve. Accordingly, the shapes of the impaction struts and of the stabilizer may include portions with a bicuspid shape, a tricuspid shape, or a semilunar shape, and may additionally have a portion with a depression corresponding to the folding lines, depending on the valve to be treated, Due to these predetermined shapes, impactor 70, by impacting against the stabilizer 14S, is able to generate fractures along the leaflet bases (close to the annulus) and central folding lines of the valve. This is in contrast with the prior art wherein fractures are not purposely made at these critical places, rather at other places along the leaflets. This method of generating fractures along the desired fracture site, e.g., the leaflet bases (close to the annulus) and central folding lines, can provide significant improvement in the ability to efficiently fracture calcifications within a relatively short procedure time. In addition, as mentioned, impactor 70 and stabilizer 14S (FIG. 6) have predetermined shapes that self-position the device with respect to the valve.

Figure 10:
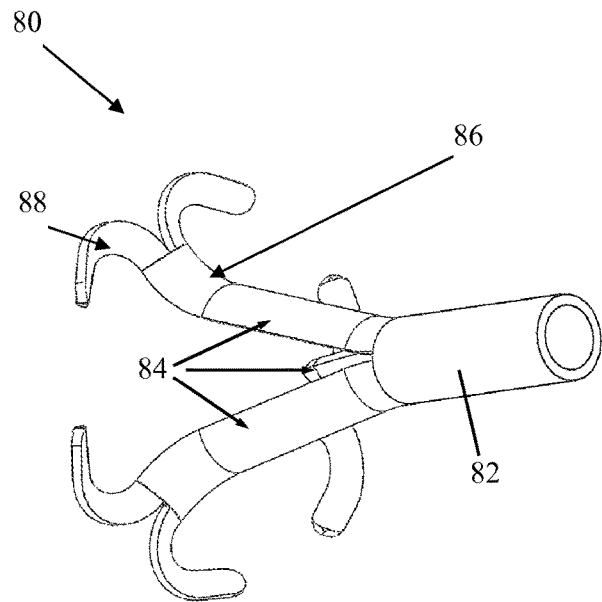
FIG. 10 is a simplified illustration of the "M" stabilizer design with a footprint similar to the stabilizer footprint shown in FIG. 6, in accordance with an embodiment of the invention.
Figure 11:
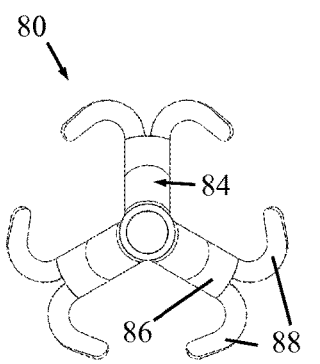
FIG. 11-12 is a simplified illustration of the top and side view of the "M" stabilizer design, in accordance with an embodiment of the invention.
Figure 12:
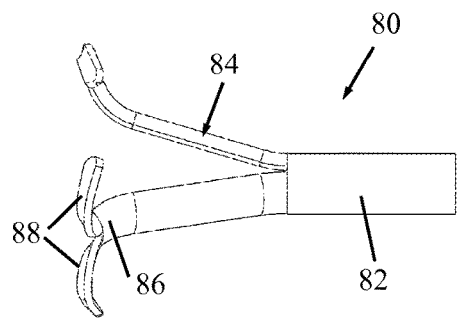

Reference is now made to FIGS. 10-12, which illustrate a stabilizer assembly 80, in accordance with an embodiment of the invention. Stabilizer assembly 80 may include a shaft 82, from which extend a plurality of arms 84 (three are shown, spaced 120° apart, in the non-limiting illustrated embodiment). Distal portions of arms 84 include a full bridge section 86 which terminates in a pair of half bridge sections 88. Stabilizer assembly 80 may be considered to have an "M" stabilizer design with a footprint similar to the stabilizer footprint presented in FIG. 6. The "M" stabilizer preferably, but not necessarily, contacts the leaflets from their aortic aspect using full bridge sections 86 and half bridge sections 88. The half bridge section 88 is positioned on the bases of the leaflets so as to counteract the impactor (such as impactor 70 of FIG. 7) in order to break calcific deposits mainly along the base of the leaflet (its connection to the aortic wall). The full bridge section 86 is positioned on the centerline of the leaflets in order to break calcific deposits mainly along the central folding line of the leaflets.

The "M" stabilizer can be positioned in various rotational positions on the valve, preferably, but not necessarily, with its full bridge section 86 along the centerline of the leaflet or with its full bridge section 86 on the commissures so that each half bridge section 88 is touching two leaflets at a time.

Figure 13:
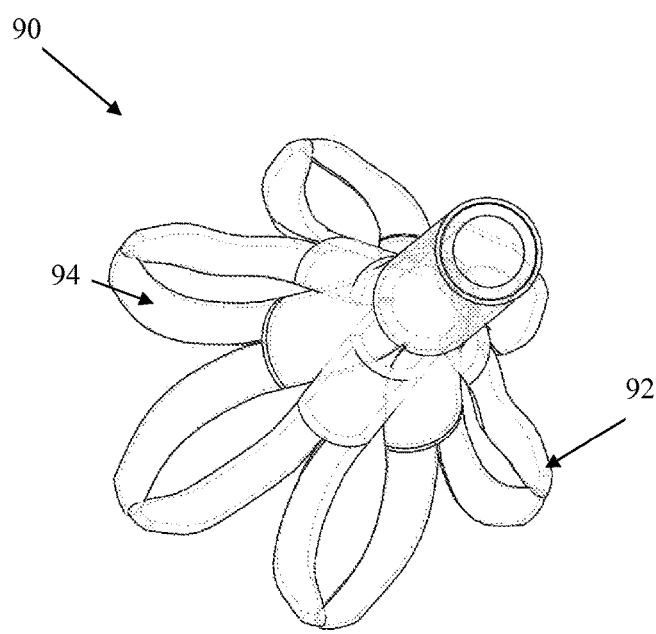
FIGS. 13-15 are simplified illustrations of the double layer stabilizer design, in accordance with an embodiment of the invention.
Figures 14, 15:
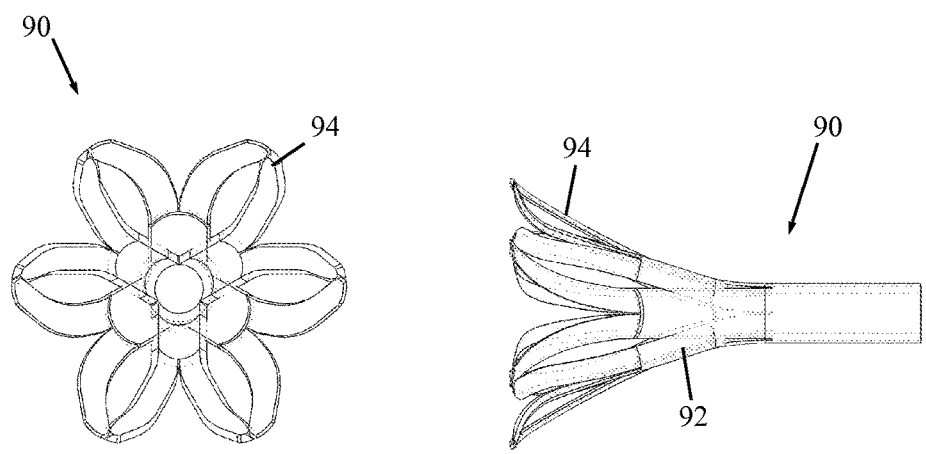

Reference is now made to FIGS. 13-15, which illustrate a stabilizer assembly 90, in accordance with another embodiment of the invention. Stabilizer assembly 90 may include a double layer stabilizer design, including an external layer 92 which pulls an internal layer 94 and forms a flower shaped stabilizer with two "petals" on each valve leaflet. The double layer stabilizer may be operated in various rotational positions and thus can achieve multiple footprints on the valve in order to generate a significant amount of calcium fractures. The double layer stabilizer is preferably positioned on the aortic aspect of the valve and is capable of fracturing calcific deposits located in the bases of the leaflets and in the central folding line of the leaflet. The extent of pulling of the external layer determines the stabilizer's diameter.

Figure 16:
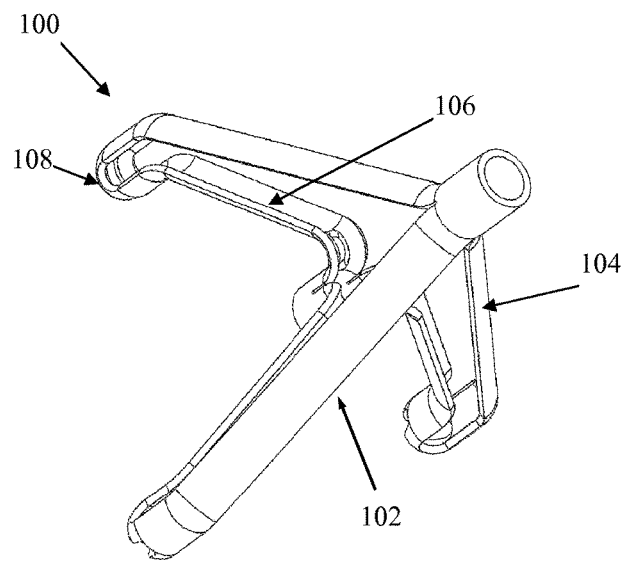
FIGS. 16-18 are simplified illustrations of a "basket" stabilizer, in accordance with an embodiment of the invention.
Figure 17:
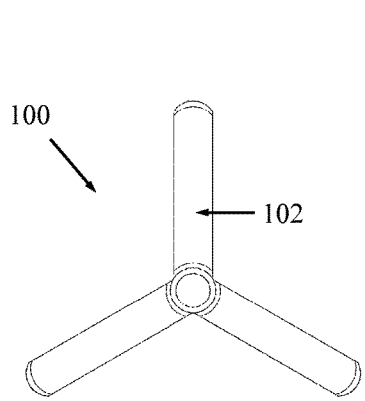
Figure 18:
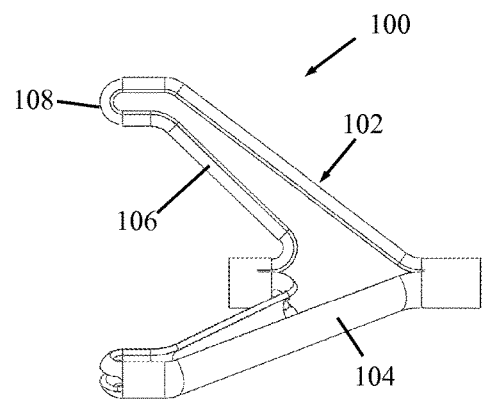

Reference is now made to FIGS. 16-18, which illustrate a stabilizer assembly 100, in accordance with another embodiment of the invention. Stabilizer assembly 100 may include a "basket" stabilizer design, including one stabilizer arm 102 on each valve leaflet. Each stabilizer arm 102 includes a proximal structural strut 104 from which extends a distal structural strut 106. A rounded stabilizing tip 108 is positioned at the junction of proximal structural strut 104 and distal structural strut 106, and another rounded stabilizing tip 108 is positioned at the junction of all the proximal structural struts 104. The "basket" design can be rotated to multiple positions and can increase and/or decrease its diameter. Hence, this stabilizer is capable of touching any point on the valve and to counteract the impact delivered by the impactor at any selected location on the valve. The "basket" stabilizing tips 108 are fully rounded and have excellent safety properties in addition to high rigidity and counteracting attributes.

Figure 19:
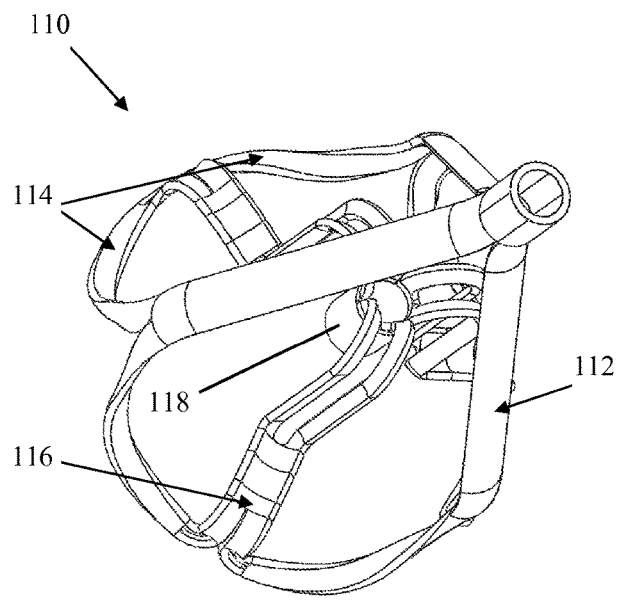
FIGS. 19-21 are simplified illustrations of a "rose" stabilizer assembly, in accordance with another embodiment of the invention.
Figure 20:
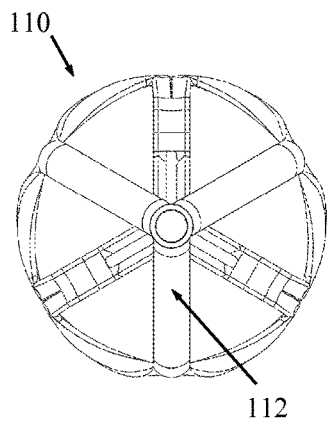
Figure 21:
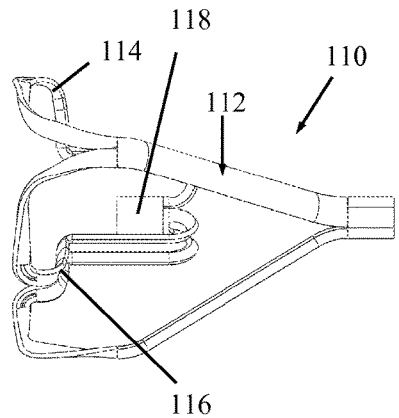

Reference is now made to FIGS. 19-21, which illustrate a stabilizer assembly 110, in accordance with another embodiment of the invention. Stabilizer assembly 110 may include a "rose" or "rose-petal" stabilizer design, including a plurality of structural struts 112 (for each valve leaflet). The structural struts 112 extend into curved, twisted, half bridge stabilizing struts 114, which in turn extend into full bridge stabilizing struts 116. A rounded stabilizing tip 118 is positioned at the junction of extensions of the full bridge stabilizing struts 116. The "rose" design can be rotated to multiple positions and can increase and/or decrease its diameter. Hence, this stabilizer is capable of touching any point on the valve and to counteract the impact delivered by the impactor at any selected location on the valve. The half bridge stabilizing struts 114 are fully rounded and have excellent safety properties in addition to high rigidity and counteracting attributes.

Figure 22:
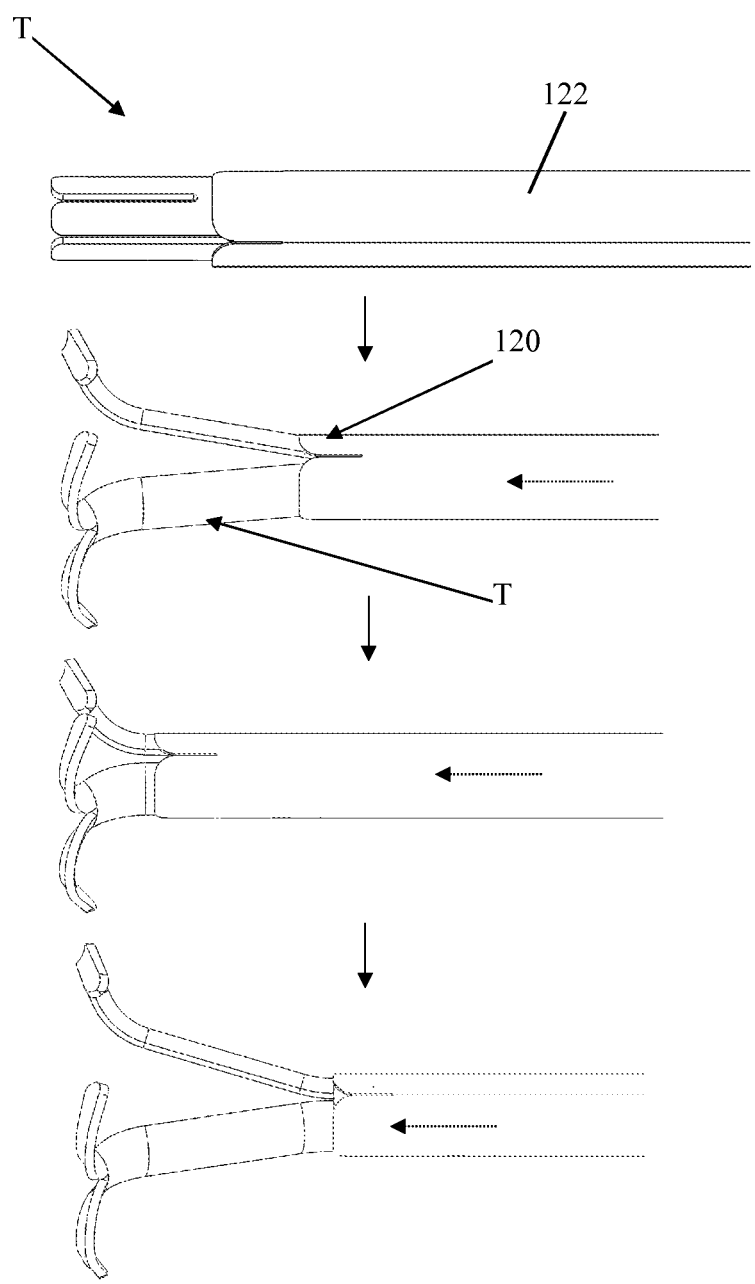
FIG. 22 is a simplified illustration of the steps of opening and closing the "M" stabilizer of FIG. 10, in accordance with an embodiment of the invention.

Reference is now made to FIG. 22, which illustrates use of an external tip 120 of a tube 122 for deploying the stabilizing assemblies of the present invention. The external tip 120 of the tube 122 initially covers a stabilizer tube T (of any of the embodiments of the invention). The external tip 120 may have an open distal end and is capable of gradually moving forward (distally) and backwards on the stabilizer and stabilizer tube T. When moving forward the external tip 120 covers more of the stabilizer structure and thus reinforces it and allows a higher counteract force. It may also be pushed forward to decrease the stabilizer diameter or to change the angle in which the stabilizer approaches the valve. All of the mentioned actions can be reversed by pulling the external tip backwards.

Figure 23:
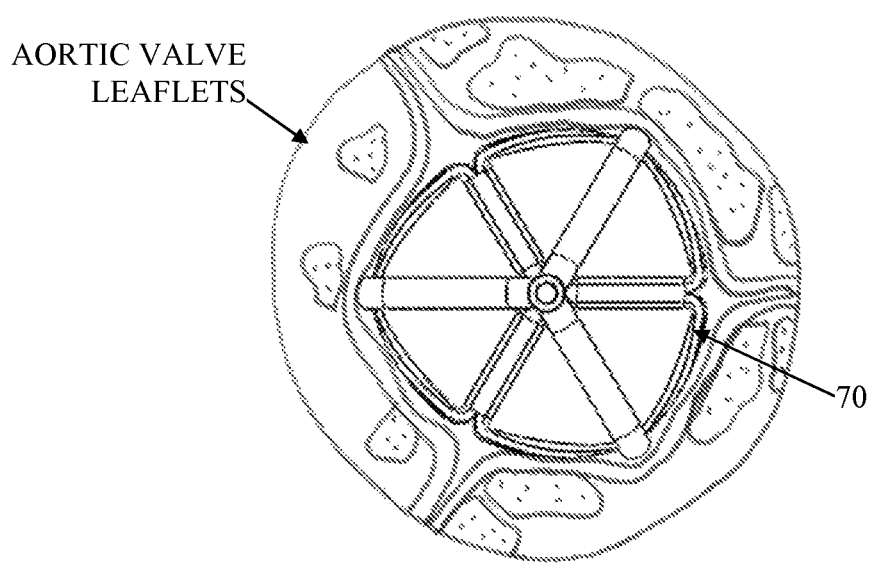
FIG. 23 is a simplified illustration of a method of using various impactor designs for dilating the valve, in accordance with an embodiment of the invention, and of a method of using various impactor designs for measuring the real valve diameter, in accordance with an embodiment of the invention.

Reference is now made to FIG. 23, which illustrates a method of using various impactor designs for increasing the open cross-sectional area of the valve during systole. In this method the impactor (such as impactor 70) is inserted in a fully or partially closed configuration through the valve in between the valve's leaflets and then is gradually dilated to increase the open cross-sectional area of the valve. This method may be used before or after impact has been delivered to the leaflets to increase the effect of valve fractures on leaflet pliability, or without delivering impact to the valve. Impactor dilation of the valve may enlarge present fractures, create new fractures, stretch the valve and its immediate surroundings, separate fused commissures and soften calcific deposits within the valve. The impactor dilation is designed so as not to obstruct blood flow from the left ventricle towards the aorta, thus making rapid pacing unnecessary in this procedure. The method of impactor dilation may also be designed for dilating other valves, such as the mitral valve, for performing angioplasty on calcified plaque or for increasing the open lumen cross-sectional area in vessels and other lumens in the human anatomy FIG. 23 also illustrates a method of using various impactor designs for measuring the real valve diameter, in accordance with an embodiment of the invention. In this method the impactor (such as impactor 70) is inserted in a fully or partially closed configuration through the valve in between the valve's leaflets, and then is gradually dilated to increase its size until the valve is fully open. Once the valve is open to a sufficient extent, the impactor diameter (and thus the open cross-sectional diameter) can be viewed on the operating catheter handle. The method of impactor sizing gives a real, in-situ measurement of the valve and may help in determining future prosthesis sizes or in other optional therapies. The method of impactor sizing may also be designed for sizing other valves, such as the mitral valve, for measuring the surroundings of the valve (annulus, aorta), for measuring open lumen cross-sectional areas in healthy or partially obstructed vessels or for measuring the cross-sectional area of other lumens in the human anatomy.

Figure 24A:
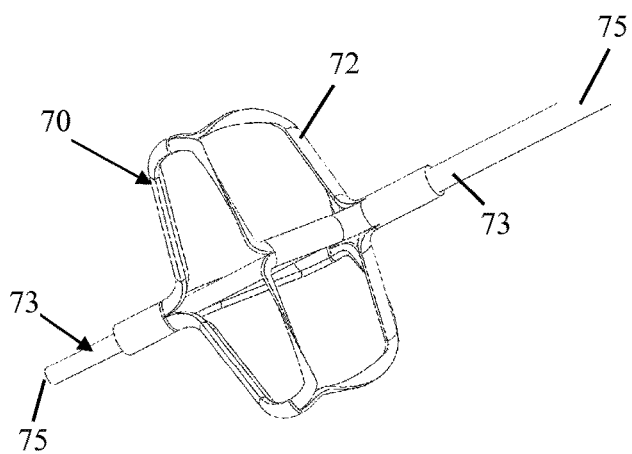
FIGS. 24A-24B are simplified illustrations of an inner lumen of an impactor and delivery system, and its ability to take pressure measurements from the ventricular and aortic aspects of the aortic valve, in accordance with an embodiment of the invention.
Figure 24B:
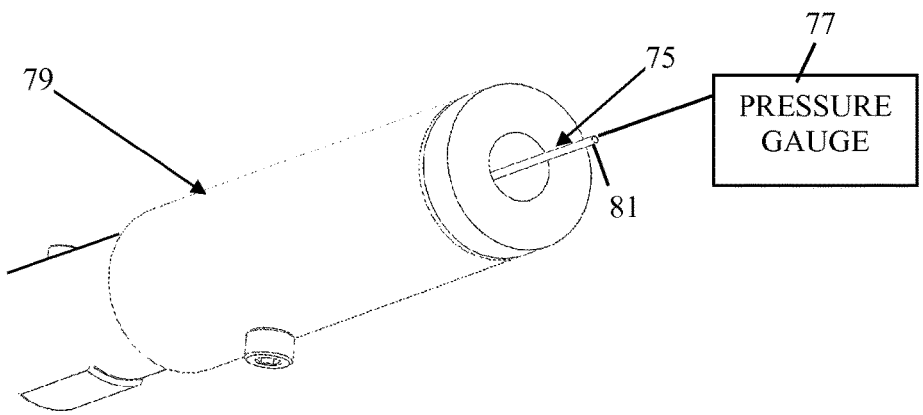

Reference is now made to FIGS. 24A-24B, which illustrate the inner lumen of the impactor and delivery system, and demonstrates its ability to take pressure measurements from the ventricular and aortic aspects of the aortic valve. The impaction struts 72 of impactor 70 may be mounted around an internal sealed shaft 73. The internal sealed shaft 73 has a lumen 75 that extends from the proximal to the distal part of the catheter. In the proximal side, lumen 75 continues all the way to a delivery system handle 79, wherein lumen 75 may terminate in a connection point 81, which is connected to a pressure gauge 77 that indicates the pressure present in the distal part of lumen 75.

By allowing blood to enter the lumen the pressure gauge is affected by the blood pressure and thus can indicate the real-time blood pressure at the distal end of the internal sealed shaft. The use of this method makes it unnecessary to use a pigtail for left ventricle pressure measurements. The method of internal sealed shaft pressure measurement may also be designed for measuring the pressure across other valves, such as the mitral valve, or for measuring the pressure in other lumens in the human anatomy.

Figure 25:
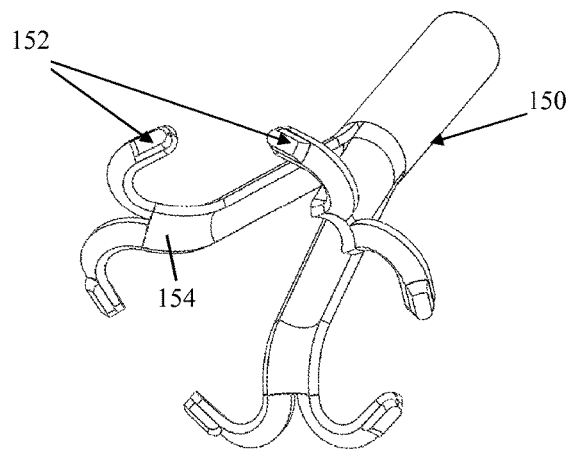
FIGS. 25-27 are simplified illustrations of a stabilizer assembly with cushions or shock absorbers on stabilizing struts, in accordance with an embodiment of the invention.
Figure 26:
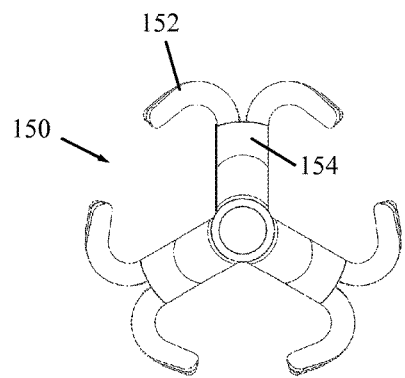
Figure 27:
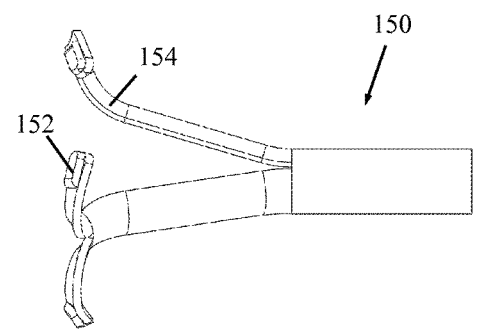

Reference is now made to FIGS. 25-27, which illustrate a stabilizer assembly 150 with cushions or shock absorbers 152 on stabilizing struts 154, in accordance with an embodiment of the invention. Shock absorbers 152 are disposed on the distal portions of half bridge stabilizer sections. Shock absorbers 152 may be made of any suitably soft material, such as an elastomer or soft plastic, for example.

Figure 28:
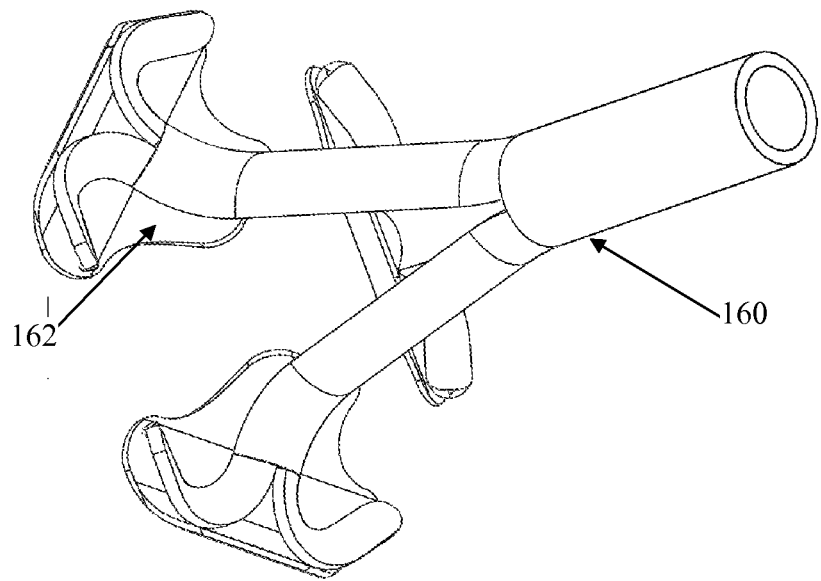
FIGS. 28-30 are simplified illustrations of a stabilizer assembly with cushions or shock absorbers on stabilizing struts, in accordance with another embodiment of the invention.
Figure 29:
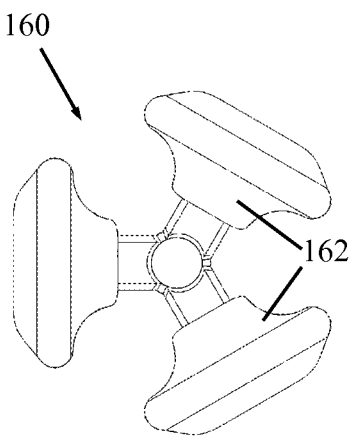
Figure 30:
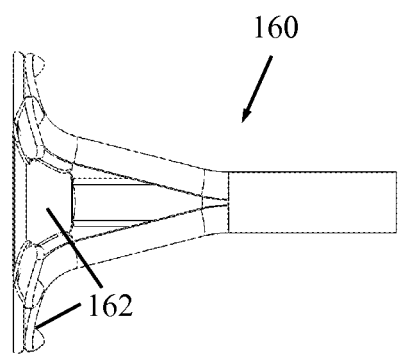

Reference is now made to FIGS. 28-30, which illustrate a stabilizer assembly 160 with cushions or shock absorbers 162 on stabilizing struts, in accordance with another embodiment of the invention. In this embodiment, shock absorbers 162 are disposed as full "webs" on the half bridge stabilizer sections and the bridge stabilizer sections.

Figure 31:
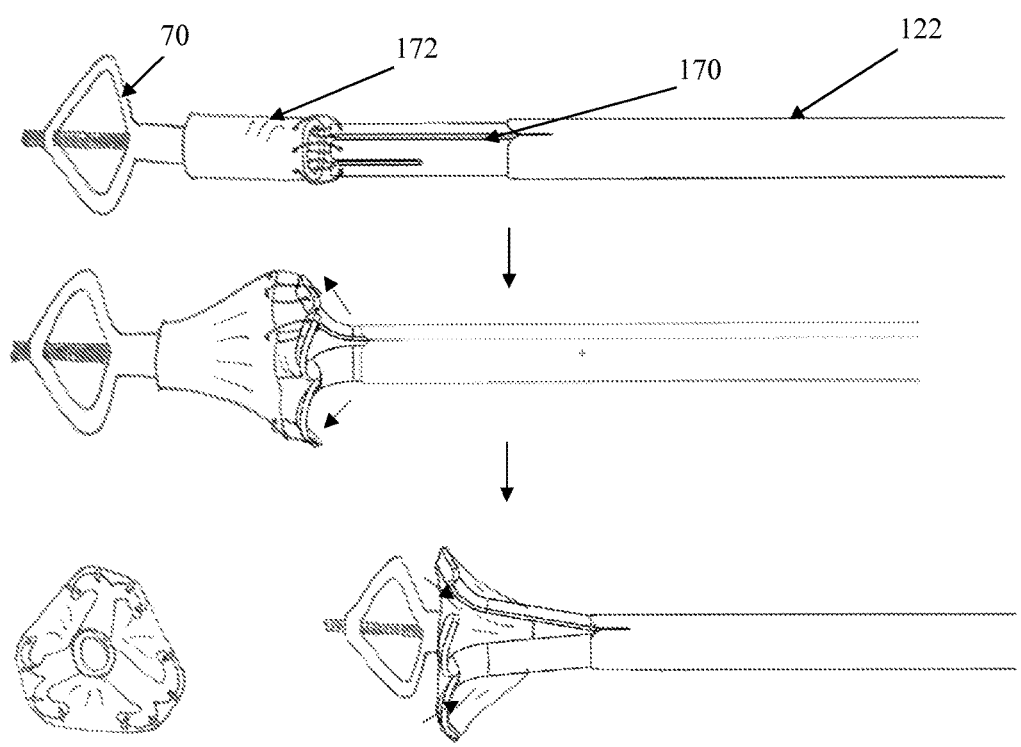
FIG. 31 is a simplified illustration of a stabilizer assembly with cushions or shock absorbers on stabilizing struts, which can also be used for embolic capturing, in accordance with yet another embodiment of the invention.

Reference is now made to FIG. 31, which illustrates a stabilizer assembly 170 with cushions or shock absorbers 172 on stabilizing struts, in accordance with yet another embodiment of the invention. In this embodiment, shock absorbers 172 are constructed from a stretchable material, such as a stretchable plastic, that extends outwards like an umbrella or canopy when deployed out of the stabilizer tube 122. These absorbers can also be used as capturing means in case embolic debris is created on the aortic aspect of the valve during valve manipulation or impact.

Figure 32:
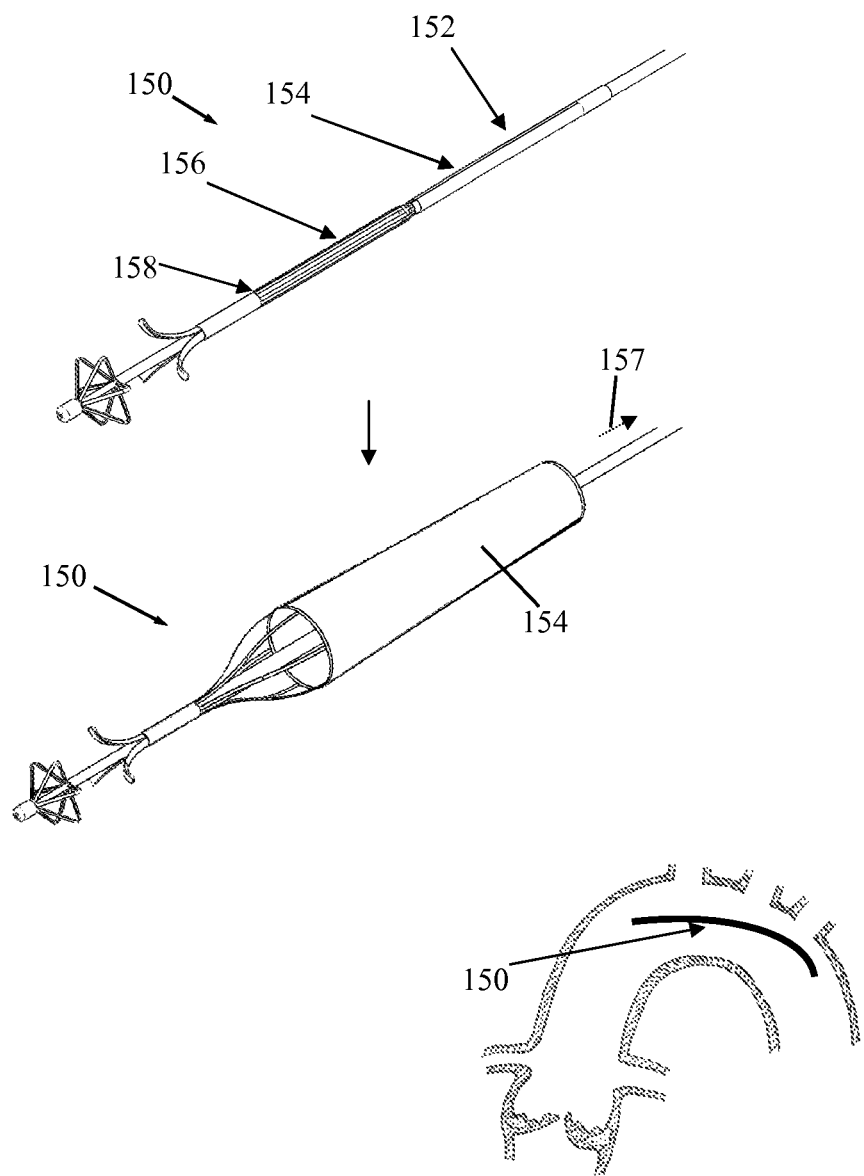
FIG. 32 is a simplified illustration of a "parachute" embolic protection structure, capable of deflecting debris in the blood stream away from the carotid-aortic arch junction, in accordance with an embodiment of the invention.

Reference is now made to FIG. 32, which illustrates a "parachute" embolic protection structure (filter) 150, capable of deflecting debris in the blood stream away from the carotid-aortic arch junction. The "parachute" embolic filter 150 includes an external operating tube 152, a porous sleeve (the "parachute") 154 and cords 156 that connect the "parachute" 154 at a connection area 156 to the distal part of the external tube 152. The embolic protection filter 150 is activated once the operating tube 152 is pulled backwards in the direction of arrow 157 (towards the proximal side); the parachute sleeve 154 then opens due to the blood flow. Once the "parachute" 154 is open the aortic arch is covered by the porous filter 150 and the blood that flows into the carotid arteries is filtered. The debris, if present, is thus deflected to the descending aorta, making it impossible for the debris to obstruct blood flow to the brain.

Figure 33:
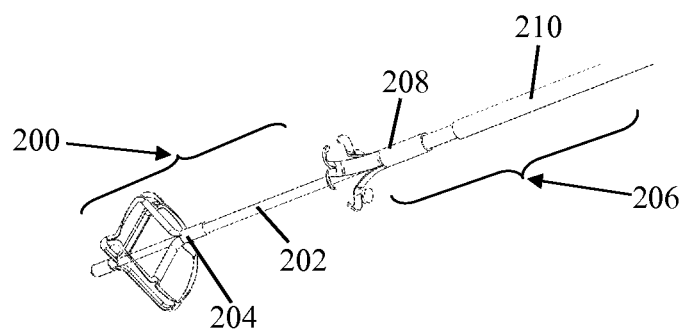
FIG. 33 is a simplified illustration of transmitting impact across the delivery system to the impactor, in accordance with an embodiment of the invention.

Reference is now made to FIG. 33, which illustrates the components and methods of transmitting impact across the delivery system to the impactor. In this figure two layers (also called impactor and stabilizer assemblies) are presented: the internal layer 200 consisting of an internal tube 202 and impactor tube 204, and the external layer 206 consisting of a stabilizer tube 208 and an external tube 210. Each layer is designed to effectively counteract the other.

The internal layer 200 is preferably constructed of a material with negligible elongation, such as but not limited to, a bundle of stainless steel wires. The external layer 206 is preferably constructed of a material with negligible compression, such as but not limited to, a braided stainless steel mesh coated with a polymer, such as polyamide 12 (e.g., VESTAMID). Friction between the layers may be minimized by coating the inner surface of the external layer 206 with polytetrafluoroethylene.

The internal layer 200 is initially pre-tensioned against the external layer 206, with the valve tissue pinched (preferably gently pinched) therebetween. This creates a static pre-loaded mechanical force on both layers. Impact is delivered by a rapid and short deflection of the internal layer 200 towards the external layer 206. The internal layer 200 is rapidly pulled, such as by mechanical impact, so that the internal layer 200 is further squeezed against the external layer 206. This causes the impactor to impact the valve which then encounters the external layer's counteracting force. The counteracting forces of the external and internal layers result in fractured calcific deposits along and in proximity to the footprints of the impactor and stabilizer. The ability to transmit impact across a full catheter is due to, inter alia, the internal layer's negligible elongation, the external layer's negligible compression, both layers' resistance to impact and negligible friction between layers. The internal layer's negligible elongation means the internal layer transmits the full force of the impact with negligible losses due to strain or stress on the internal layer's material. The external layer's negligible compression means the external layer can act as an excellent anvil to bear the brunt of the impact with negligible losses due strain or stress on the external layer's material. Another parameter that helps to achieve efficacious impact is both layers' pre-tensioning towards each other.

What is claimed is:

1. A device for fracturing calcifications in heart valves comprising:
a stabilizer assembly and an impactor assembly assembled on and deployed by a delivery system, wherein said delivery system is operable to cause relative motion between said impactor assembly and said stabilizer assembly with sufficient energy so as to fracture a calcification located in tissue which is sandwiched between said stabilizer assembly and said impactor assembly said impactor assembly comprising a biasing device;
wherein said impactor assembly and said stabilizer assembly have shaped impact delivery portions configured to have a shape in accordance with the tissue which is sandwiched between said stabilizer assembly and said impactor assembly, and wherein said stabilizer assembly comprises an external layer and said impactor assembly comprises an internal layer, said external and internal layers being movable with respect to each other, such that moving one of said external and internal layers with respect to the other changes the shape of said stabilizer assembly, and wherein said internal layer comprises an internal tube and an impactor tube, and said external layer comprises a stabilizer tube and an external tube, and wherein said internal layer and said external layer are initially pre-tensioned towards each other.

2. The device according to claim 1, wherein said shaped impact delivery portions are arranged to be located in proximity to valve leaflet bases or radial/central folding lines of valve leaflets.

3. The device according to claim 1, wherein said stabilizer assembly comprises a plurality of stabilizer arms, and wherein each stabilizer arm comprises a proximal structural strut from which extends a distal structural strut, and a rounded stabilizing tip is positioned at a junction of each of said proximal and distal structural struts.

4. The device according to claim 1, wherein said stabilizer assembly comprises a plurality of structural struts that extend into curved, twisted, half bridge stabilizing struts, which in turn extend into full bridge stabilizing struts.

5. The device according to claim 1, further comprising an embolic protection structure.

6. The device according to claim 1, wherein said internal layer is constructed of a material with negligible elongation and said external layer is constructed of a material with negligible compression.

* * * * *